United States Patent [19]
Brockhaus

[11] Patent Number: 6,092,428
[45] Date of Patent: Jul. 25, 2000

[54] DEVICE FOR DETERMINING THE PHASE COMPONENT OF A CONDUCTIVE MEDIUM IN A DUCT

[75] Inventor: Helmut Brockhaus, Dinslaken, Germany

[73] Assignee: Krohne Messtechnik GmbH & Co. KG, Duisburg, Germany

[21] Appl. No.: 08/981,246
[22] PCT Filed: Apr. 17, 1997
[86] PCT No.: PCT/EP97/01936
§ 371 Date: Dec. 17, 1997
§ 102(e) Date: Dec. 17, 1997
[87] PCT Pub. No.: WO97/39313
PCT Pub. Date: Oct. 23, 1997

[30] Foreign Application Priority Data

Apr. 17, 1996 [DE] Germany .................. 196 15 140

[51] Int. Cl.[7] .................................................. G01F 1/58
[52] U.S. Cl. .................................................. 73/861.14
[58] Field of Search .................. 73/861.14, 861.08, 73/861.11, 861.12, 861.16, 861.17

[56] References Cited

U.S. PATENT DOCUMENTS

| | | | |
|---|---|---|---|
| 3,489,007 | 1/1970 | Cushing | 73/861.14 |
| 3,991,612 | 11/1976 | Mannherz et al. | 73/861.17 |
| 3,999,443 | 12/1976 | Appel et al. | 73/861.17 |
| 4,036,052 | 7/1977 | Searle | 73/861.17 |
| 4,483,201 | 11/1984 | Haug | 73/861.12 |
| 4,785,672 | 11/1988 | Picone | 73/861.14 X |
| 4,972,722 | 11/1990 | Hansen et al. | 73/861.17 |
| 5,018,391 | 5/1991 | Doll | 73/861.17 |
| 5,400,660 | 3/1995 | Doll | 73/861.17 |
| 5,421,210 | 6/1995 | Kobayshi et al. | 73/861.12 |
| 5,544,532 | 8/1996 | Brown | 73/861.16 |
| 5,625,155 | 4/1997 | Yoshida | 73/861.16 X |
| 5,641,914 | 6/1997 | Doll | 73/861.17 |

FOREIGN PATENT DOCUMENTS

| | | |
|---|---|---|
| 0 514 964 | 11/1992 | European Pat. Off. . |
| 0 547 751 | 6/1993 | European Pat. Off. . |
| 0 626 567 | 11/1994 | European Pat. Off. . |
| 38 10 034 | 10/1989 | Germany . |
| 195 31 124 | 2/1997 | Germany . |
| 08086674 | 4/1996 | Japan . |

OTHER PUBLICATIONS

Kapazitive Fullstandsmessverfahren, J. Fehrenbach, (1990) pp. 102–111.

*Primary Examiner*—Max Noori
*Assistant Examiner*—Jewel V. Thompson

[57] ABSTRACT

A device for determining the level of a conducting medium in a line, in particular for use in connection with a magnetically-inductive flowmeter, with at least one capacitor plate, with an insulation layer between the capacitor plate and the medium and with a control and evaluation circuit, the control and evaluation circuit acting upon the capacitor plate with an alternating voltage. The device is improved by having the control and evaluation circuit determine the capacitance between the capacitor plate and the medium as a measure for the level.

10 Claims, 2 Drawing Sheets

DEVICE FOR DETERMINING THE PHASE COMPONENT OF A CONDUCTIVE MEDIUM IN A DUCT

The invention concerns a device for determining the level of a conducting medium in a line, in particular for use in connection with a magnetic inductive flowmeter, with at least one capacitor plate, with an insulation layer between the capacitor plate and the medium, and with a control and evaluation circuit, the control and evaluation circuit acting upon the capacitor plate with an alternating voltage.

BACKGROUND OF THE INVENTION

The invention is particularly suited for use in a magnetic inductive flowmeter (MIF), in particular in an MIF with capacitively coupled electrodes. In the case of this combination, the capacitively coupled electrodes needed for the flow measurement by means of the MIF are used simultaneously as capacitor plates for determining the level. Furthermore, the combination of the present invention with an MIF is advantageous because it is not possible to distinguish between a reduced flow rate and a reduced level of the conducting medium from the measurement signal of an MIF.

Devices for determining the level of a conducting medium in a line in connection with an MIF with galvanically coupled electrodes are known from the prior art. These are also called idling identifications, i.e., the device can tell if the line is running dry. In the case of such an idling identification, the normal flow measurement of the MIF is used at the same time to check if the line is completely filled with the conducting medium. However, the operating principle of these known idling identifications fundamentally differs from that of the invention.

The processes and devices for determining the level of a medium in a line, known from European Offenlegungsschriften 0 514 964 and 0 547 751 as well as from the republished German Offenlegungsschrift 195 31 124, constitute the starting point of the present invention. In the case of these known processes and devices, the current between two capacitor plates always is evaluated for determining the level. This leads, as is evident from the above-mentioned prior art, to a division of the capacitor plates and relatively expensive control of the capacitor plates and evaluation of the measurement signals obtained. This problem results from the fact that the current between two capacitor plates is determined essentially by the electrical properties of the medium, therefore in particular the dielectric constant $\epsilon$ and the electric conductivity $\sigma$.

SUMMARY OF THE INVENTION

Thus the object of the invention is to make available a device for determining the level of a conducting medium in a line, which is designed simply and operates at least essentially independent of the electrical properties of the conducting medium.

The object indicated and derived previously is solved in accordance with the invention in that the control and evaluation circuit determines the capacitance between the capacitor plate and the medium as a measure for the level. Therefore, the phase portion of the conducting medium may be determined advantageously with the device in accordance with the invention by means of a corresponding control only of one capacitor plate. This capacitor plate at the same time also can form a capacitively coupled electrode of an MIF. In the case of a completely filled line, a capacitance is formed between the capacitor plate with a surface A and the conducting medium. Now if the line no longer is completely filled, this results in a smaller capacitance $C_{Me\beta}$, which is proportional to a smaller surface A'. The smaller surface A' is obtained by projection of the surface A from the outside of the line onto the inside and consideration of only a part of this surface, which is wetted with the conducting medium. If the average thickness of the insulation layer between the capacitor plate and the conducting medium is designated as d and the dielectric constant of this layer is designated as $\epsilon$, the following is obtained for $C_{Me\beta}$:

$$C_{Me\beta} = \varepsilon \frac{A}{d}$$

and for $C'_{Me\beta}$:

$$C'_{Me\beta} = \varepsilon \frac{A'}{d}$$

From this it is recognized that the capacitance between the capacitor plate and the medium is suited directly as a measure for the level of the conducting medium in the line.

According to a first development of the teaching in accordance with the invention, the control and evaluation circuit performs a threshold value decision by means of the measured capacitance between the capacitor plate and the medium. An open-circuit signal is emitted in the known way in the case of dropping below the threshold value.

Alternative or cumulative to the open-circuit identification known by itself, the teaching in accordance with the invention is further developed by having the control and evaluation circuit evaluate the capacitance between the capacitor plate and the medium quantitatively, that is, it emits a signal proportional to the level of the medium in the line. Thus, in the case of a combination of the device in accordance with an MIF, even in the case of an only partially filled line, it is assured that the amount of the flow can be determined correctly.

According to a further development of the teaching in accordance with the invention, if the alternating voltage is applied between two capacitor plates, the already minor influence of the electrical properties of the conducting medium on the measurement signal of the device in accordance with the invention is reduced further, since the charge transport within the fluid has to take place only on a relatively short section.

According to an alternative development of the teaching in accordance with the invention, the alternating voltage is applied respectively between a capacitor plate and a reference potential, with which the medium is connected by means of a grounding means. This development ensures a realization of the device in accordance with the invention with only one capacitor plate.

The connection with the reference potential, necessary in the case of the last described development, can take place conventionally via grounding rings or metal pipe pieces, or, according to the further development of the theory in accordance with the invention, via capacitively coupled electrodes isolated from the medium, which are connected with the reference potential. In particular, this alternative is to be preferred when the medium is chemically aggressive with respect to metals, since contact of the grounding means with the medium is avoided herewith.

In the case of the last described alternative development, it is to be noted further that the alternating current resistance of the capacitance between the capacitor plate and the medium at the frequency $f_{Test}$ of the alternating voltage is at most on the order of magnitude of the ohmic resistance $R_{Medium}$ of the medium with respect to the reference potential. Expressed as a formula, this is approximately:

$$R_{Medium} \leq \frac{1}{2\pi f_{Test} C_{Me\beta}}$$

This measure ensures that the charge transport through the conducting medium has only an insignificant negative effect on the measurement result, in which case the accuracy of the measurement signal is to be improved further by lowering the alternating current resistance of the capacitance between the capacitor plate and the medium by increasing the frequency $f_{Test}$.

The device in accordance with the invention undergoes a further development by having the capacitance between the capacitor plate and the medium form a first capacitance of a capacitive voltage divider having at least two capacitances, and having the control and evaluation circuit tap the measurement signal on the middle tap of the capacitive voltage divider. In the case of this configuration of the teaching in accordance with the invention, the alternating voltage signal $S_{Test}$ is present on the capacitance between the capacitor plate and the medium via the second capacitance of the capacitive voltage divider. Thus, the following relationship results for the voltage $U_{Test}$ evaluated by the control and evaluation circuit:

$$U_{Test} = S_{Test} \frac{C_{Test}}{C_{Test} + C'_{Me\beta}}$$

with $C_{Test}$=second capacitance of the capacitive voltage divider.

This configuration of the object in accordance with the invention is advantageous, since a possibility for measuring the capacitance between the capacitor plate and the medium, which is especially easy to implement, is made available in this way.

The last described arrangement undergoes a further advantageous development by having the second capacitance $C_{Me\beta}$ of the capacitive voltage divider be smaller than the first capacitance $C_{Me\beta}$. Then, in the case of an empty line, the voltage $U_{Test}$ is great, since $C'_{Me\beta}$ is almost equal to zero. On the other hand, in the case of a full line, the voltage $U_{Test}$ is small, since $C'_{Me\beta}$ is clearly greater than $C_{Test}$.

A small second capacitance $C_{Test}$, as proposed, may be made available especially simply without extensive circuitry by having a parasitic capacitance of the control and evaluation circuit form this second capacitance $C_{Test}$.

In particular, there are now a number of possibilities for designing and further developing the device in accordance with the invention for determining the level of a conducting medium in a line. The dependent patent claims, on the one hand, and the description of preferred embodiments in connection with the drawings, on the other hand, are to be consulted here.

DETAILED DESCRIPTION OF ILLUSTRATIVE EMBODIMENTS

Figure 1A:
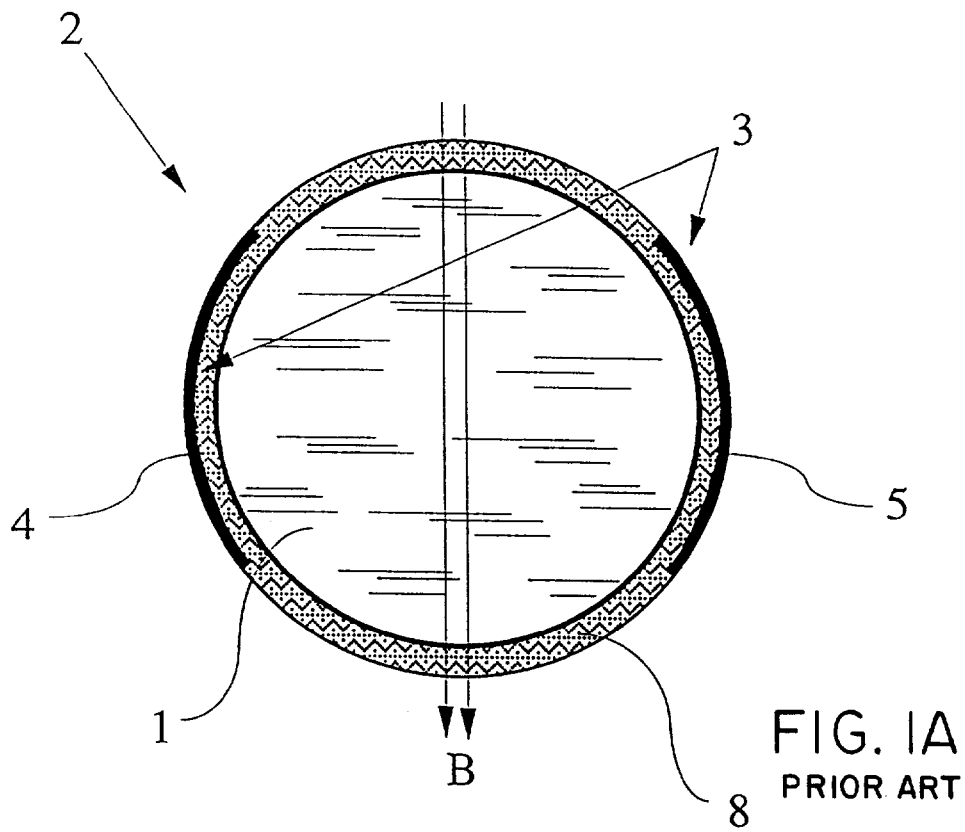
FIGS. 1A and 1B show the fundamental designs of known magnetic inductive flowmeter, both with capacitively coupled electrodes and with galvanically coupled electrodes respectively.
Figure 1B:
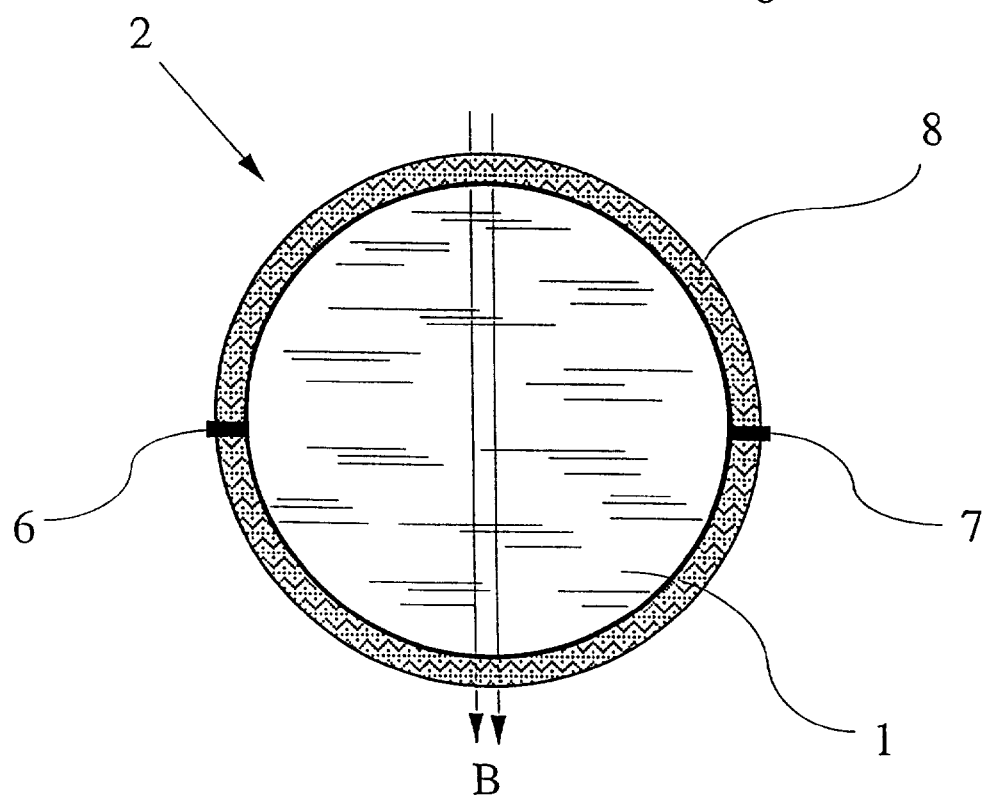

The principle of an MIF will now be explained by means of FIG. 1 of the drawings. First of all, an MIF consists of a line 2 supplying a conducting medium 1. A magnetic alternating field B with a frequency $f_{Me\beta}$, the magnetic field lines of which run essentially perpendicular to the line axis, is generated in the line 2. A charge separation in the medium is generated by the Lorenz force, depending on the flow rate v of the conducting medium. At two electrodes 4, 5, or 6, 7, the electrode axis of which is perpendicular both to the magnetic field lines as well as to the line axis, it is possible to measure an alternating voltage $U_{Me\beta}$ with the measurement frequency $f_{Me\beta}$, the amplitude of which is proportional to the flow rate of the medium 1 in the line 2. In the case of an MIF with galvanically coupled electrodes 6, 7, this voltage $U_{Me\beta}$ is tapped approximately punctual via metal contacts with the medium 1. In the case of MIF's with capacitively coupled electrodes 4, 5, which can serve simultaneously as capacitor plates in the case of the present invention, the alternating voltage $U_{Me\beta}$ is tapped capacitively between flat electrodes 4, 5, which are separated from the conducting medium by an insulation layer 8. In the case of an MIF with galvanically coupled electrodes 6, 7, the line 2 also is coated with an insulation layer 8, which, however, is interrupted by the galvanically coupled electrodes 6, 7. In the case of both versions of the known MIF, outside of the line section insulated with respect to the fluid, the conducting medium is connected with a reference potential, for example via grounding rings or metal tube pieces.

Figure 2:
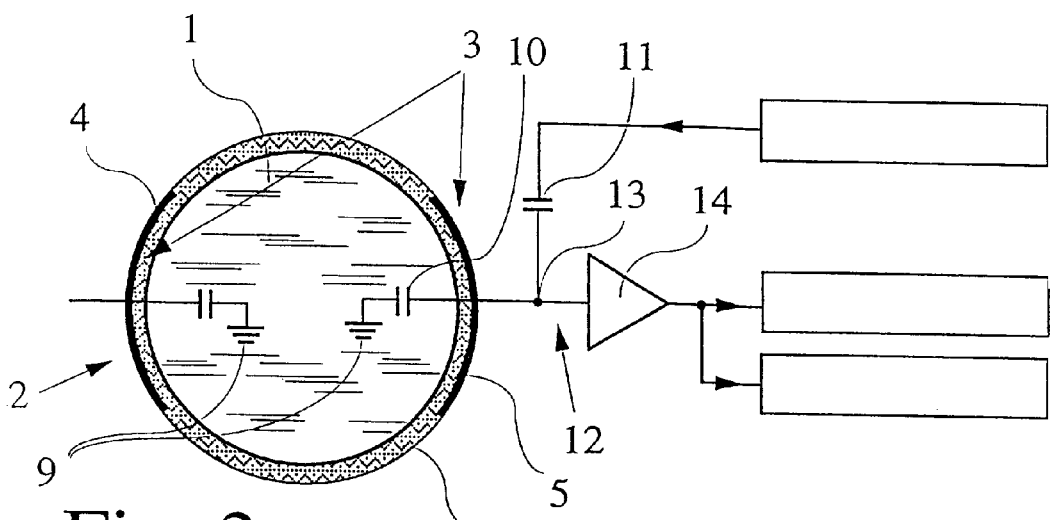
FIG. 2 shows a first embodiment of a device in accordance with the invention for determining the level of a conducting medium in a line, realized in connection with a capacitive magnetic inductive flowmeter with a completely filled line.

FIG. 2 of the drawing shows a first embodiment of a device in accordance with the invention for determining the level of a conducting medium in a line 2. In FIG. 2, the line 2 is completely filled with the conducting medium 1. Thus, the entire surface of the capacitor plates 3, therefore the electrodes 4, 5, is relevant for the capacitance between the capacitor plates 3 and the conducting medium 1. Therefore, for the capacitance $C_{Me\beta}$, the following obtains:

$$C_{Me\beta} = \varepsilon \frac{A}{d}$$

In the first embodiment of the device in accordance with the invention shown, this capacitance $C_{Me\beta}$ is determined by the fact that an alternating voltage $S_{Test}$ is applied between a capacitor plate 3, respectively between an electrode 4 or 5, and a reference potential 9, and that the medium 1 is connected with the reference potential 9 with the aid of a grounding means not shown. In the case of the first embodiment of a device in accordance with the invention shown in FIG. 2, the control and evaluation circuit is represented only for the right-hand electrode 5. If the left-hand electrode 4 also is to be used for determining the phase portion of the conducting medium 1, a corresponding control and evaluation circuit is to be connected with the left-hand electrode 4.

In the case of the first embodiment of a device in accordance with the invention shown in FIG. 2, the capacitance $C_{Me\beta}$ between the electrode 4 serving as a capacitor plate 3 and the medium 1 forms a first capacitance 10 of a capacitive voltage divider 12 having two capacitances 10, 11. The control and evaluation circuit here taps the measurement signal on the middle tap 13 of the capacitive voltage divider 12 and determines the test voltage $U_{Me\beta}$ from the signal present on the output of a buffer 14, and thus the level of the conducting medium 1 in the line 2 and the measurement voltage $U_{Me\beta}$, and therewith the flow rate V of the medium 1 in the line 2. The control and evaluation circuit then can determine the amount of flow through the line 2 from these two values. In the case of the completely filled line 2 shown, the amount of flow results in the known way from the flow rate V multiplied with the cross-section of the line 2.

Figure 3:
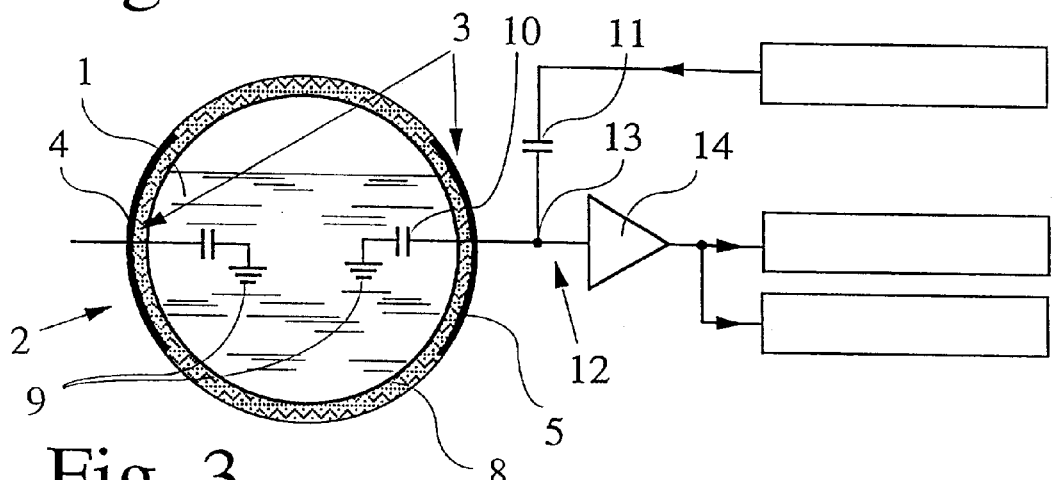
FIG. 3 shows a first embodiment of a device in accordance with the invention for determining the level of a conducting medium in a line, realized in connection with a capacitive magnetic inductive flowmeter with a partially filled line.

FIG. 3 of the drawing shows the first embodiment of a device in accordance with the invention with an only partially filled line 2. Thus, the level of the conducting medium 1 determined by the device in accordance with the invention is less than 1. This is expressed metrologically by the fact that the effective surface A' of the capacitance of the capacitor plate 3 serving as an electrode 5 is clearly smaller than the total surface of the capacitor plate 3. Thus the following obtains for the capacitance $C'_{Me\beta}$:

$$C'_{Me\beta} = \varepsilon \frac{A'}{d}$$

The capacitance $C'_{Me\beta}$ in FIG. 3 again forms the first capacitance 10 of a voltage divider 12. The control and evaluation circuit determines the capacitance between the capacitor plate 3 and the medium 1, as already described by means of FIG. 2. In the case of an only partial filling of the line 1, as shown in FIG. 3, the amount of the medium 1 flowing through the line 2 results from the flow rate V, multiplied with the cross-section of the line 2 and the level of the conducting medium 1, which can be determined from the capacitance $C'_{Me\beta}$.

Figure 4:
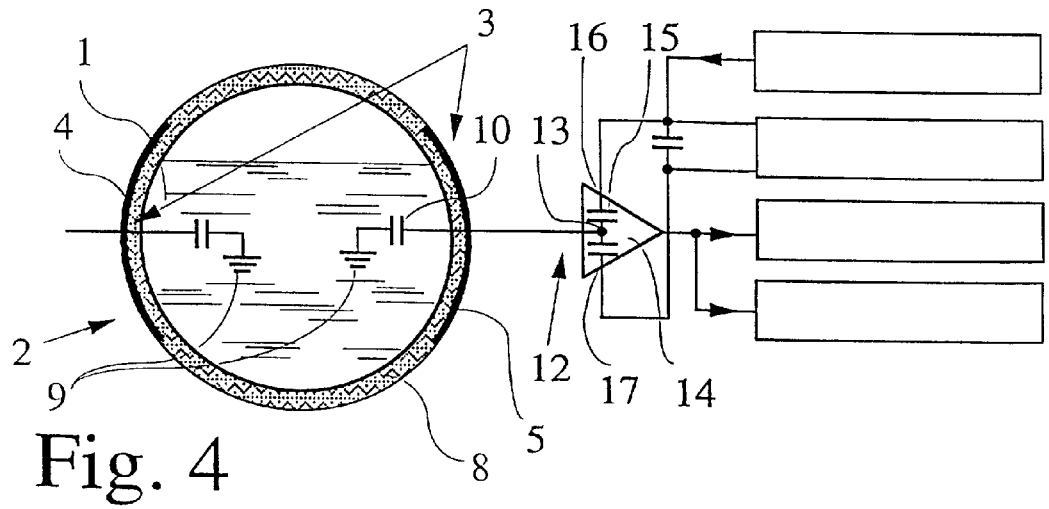
FIG. 4 shows a second embodiment of a device in accordance with the invention for determining the level of a conducting medium in a line, realized in connection with a capacitive magnetic inductive flowmeter with a partially filled line.

FIG. 4 of the drawing shows a second embodiment of a device in accordance with the invention, in the case of which a parasitic capacitance 15 of the buffer 14 of the control and evaluation circuit forms the second capacitance of a capacitive voltage divider 12. The parasitic capacitance 15 in this case is formed by a parasitic capacitor between the input of the buffer 14 and the supply connections 16, 17 thereof. Otherwise, the mode of operation of the second embodiment of a device in accordance with the invention shown in FIG. 4 corresponds with the first embodiment shown in FIGS. 2 and 3.

If the alternating voltage, as already explained in the general description, is introduced between two capacitor plates via a difference signal, the test voltage in this case is tapped between two buffers. Otherwise the function essentially corresponds with that of is the embodiments described in FIGS. 2 to 4.

In the case of the operation of a device in accordance with the invention for determining the level of a conducting medium 1 in a line 2, in connection with a magnetic inductive flowmeter, as shown in FIGS. 2 to 4, it is to be observed that the alternating voltage applied to the capacitor plates by the control and evaluation circuit must have a frequency $f_{Me\beta}$ different from the frequency $f_{Me\beta}$ of the magnetic alternating field B.

What is claimed is:

1. A device for determining the level of a conducting medium (1) in a line (2), for use in connection with a magnetic inductive flowmeter, with at least one capacitor plate (3), with an insulation layer (8) between the capacitor plate (3) and the medium (1) and with a control and evaluation circuit, the control and evaluation circuit acting on the capacitor plate (3) with an alternating voltage, wherein the control and evaluation circuit determines the capacitance between the capacitor plate (3) and the medium (1) as a measure for the level.

2. The device in accordance with claim 1, wherein the control and evaluation circuit makes a threshold value decision by means of the capacitance between the capacitor plate (3) and the medium (1).

3. The device in accordance with claim 1 or 2, wherein the control and evaluation circuit quantitatively evaluates the capacitance between the capacitor plate (3) and the medium (1).

4. The device in accordance with claim 3, wherein the alternating voltage is applied between two capacitor plates (3).

5. The device in accordance with claim 3, wherein the alternating voltage is applied respectively between a capacitor plate (3) and a reference potential (9) and the medium (1) is connected with the reference potential (9) by means of a grounding means.

6. The device in accordance with claim 5, wherein the medium (1) is coupled with the reference potential (9) via capacitively coupled electrodes which are isolated from the medium (1).

7. The device in accordance with claim 5, wherein the alternating current resistance of the capacitance between the capacitor plate (3) and the medium (1) at the frequency of the alternating voltage is at most on the order of magnitude of the ohmic resistance of the medium (1) with respect to the reference potential (9).

8. The device in accordance with claim 1, wherein the capacitance between the capacitor plate (3) and the medium (1) forms a first capacitance (10) of a capacitive voltage divider (12) having at least two capacitances (10, 11), and the control and evaluation circuit taps the measurement signal on a middle tap (13) of the capacitive voltage divider (12).

9. The device in accordance with claim 8, wherein the second capacitance (11) of the capacitive voltage divider (12) is smaller than the first capacitance (10).

10. The device in accordance with claim 8 or 9, wherein a parasitic capacitance (15) of the control and evaluation circuit forms the second capacitance.

* * * * *